US012601012B2

(12) United States Patent
Dai et al.

(10) Patent No.: US 12,601,012 B2
(45) Date of Patent: Apr. 14, 2026

(54) COMPOSITION FOR DETECTING PATHOGENS, AND KIT AND METHOD THEREFOR

(71) Applicant: SANSURE BIOTECH INC., Changsha (CN)

(72) Inventors: Lizhong Dai, Changsha (CN); Deyong Tan, Changsha (CN); Zhongping Deng, Changsha (CN); Jia Liu, Changsha (CN); Xiaomei Ren, Changsha (CN); Xing Cheng, Changsha (CN); Qingzhi Sun, Changsha (CN)

(73) Assignee: Sansure Biotech Inc., Changsha (CN)

( * ) Notice: Subject to any disclaimer, the term of this patent is extended or adjusted under 35 U.S.C. 154(b) by 840 days.

(21) Appl. No.: 17/929,563

(22) Filed: Sep. 2, 2022

(65) Prior Publication Data

US 2022/0411852 A1 Dec. 29, 2022

Related U.S. Application Data

(63) Continuation of application No. PCT/CN2020/096941, filed on Jun. 19, 2020.

(30) Foreign Application Priority Data

Mar. 13, 2020 (CN) .......................... 202010177556.3

(51) Int. Cl.
*C12Q 1/68* (2018.01)
*C07H 21/04* (2006.01)
*C12Q 1/686* (2018.01)
*C12Q 1/689* (2018.01)
*C12Q 1/70* (2006.01)

(52) U.S. Cl.
CPC ............. *C12Q 1/689* (2013.01); *C12Q 1/686* (2013.01); *C12Q 1/705* (2013.01)

(58) Field of Classification Search
None
See application file for complete search history.

(56) References Cited

U.S. PATENT DOCUMENTS

2007/0036721 A1 2/2007 Zinn et al.

FOREIGN PATENT DOCUMENTS

| CN | 103074448 A | 5/2013 |
| CN | 105624311 A | 6/2016 |
| CN | 106566882 A | 4/2017 |
| CN | 107630098 A | 1/2018 |
| CN | 109504805 A | 3/2019 |
| CN | 110607379 A | 12/2019 |
| CN | 111041130 A | 4/2020 |
| WO | WO-2018005710 A1 * | 1/2018 ........ B01L 3/502715 |
| WO | 2018141907 A1 | 8/2018 |

OTHER PUBLICATIONS

The State Intellectual Property Office of People's Republic of China, Application No. or Publication No. 202010177556.3, First Office Action, Apr. 27, 2020.
European Supplementary Search Report, Application No./Patent No. 20924101. 7-1118 / 4006172 PCT/CN202009694, Nov. 11, 2022.
PCT International Search Report, International application No. PCT /CN2020/096941, Dec. 17, 2020.
PCT Written Opinion of the International Searching Authority, International application No. PCT /CN2020/096941, Dec. 17, 2020.
Fan Huan, et al, Title of the article: Application of multiplex PCR combined with invasive reaction and chromogenic reaction catalyzed by gold nanoparticles in detection of encephalitis and meningitis virus, Chinese Journal of Zoonoses, vol. 33, pp. 991-995, Nov. 30, 2017, Fujian, China.
Steven J. Read, et al., Title of the article: Aseptic Meningitis and Encephalitis the Role of PCR in the Diagnostic Laboratory, Journal of Clinical Microbiology, vol. 35, pp. 691-696, Mar. 31, 1997, Washington.

* cited by examiner

*Primary Examiner* — Jeanine A Goldberg
(74) *Attorney, Agent, or Firm* — Flener IP & Business Law

(57) ABSTRACT

Provided is a composition for detecting multiple encephalitis/meningitis/respiratory pathogens. The composition includes primer sequences for the pathogens as shown in SEQ ID NOs: 1-7, 9-23 and 25-32, in which SEQ ID NOs: 1-7 and 9-16 carry fluorescent reporter groups. In addition, the present invention further provides a use of the foregoing composition in the preparation of a kit, and a related kit and a method for using the same.

19 Claims, 3 Drawing Sheets
Specification includes a Sequence Listing.

SEQUENCE LISTING

```
Sequence total quantity: 32
SEQ ID NO: 1              moltype = DNA  length = 22
FEATURE                   Location/Qualifiers
source                    1..22
                          mol_type = other DNA
                          note = Haemophilus influenzae forward primer
                          organism = synthetic construct
SEQUENCE: 1
caccagaata caacatcgca tt                                          22

SEQ ID NO: 2              moltype = DNA  length = 21
FEATURE                   Location/Qualifiers
source                    1..21
                          mol_type = other DNA
                          note = Streptococcus pneumoniae forward primer
                          organism = synthetic construct
SEQUENCE: 2
aaccacgagt aagagtgatg a                                           21

SEQ ID NO: 3              moltype = DNA  length = 21
FEATURE                   Location/Qualifiers
source                    1..21
                          mol_type = other DNA
                          note = Neisseria meningitidis forward primer
                          organism = synthetic construct
SEQUENCE: 3
aattctgccg taagccgcat c                                           21

SEQ ID NO: 4              moltype = DNA  length = 23
FEATURE                   Location/Qualifiers
source                    1..23
                          mol_type = other DNA
                          note = Listeria monocytogenes forward primer
                          organism = synthetic construct
SEQUENCE: 4
aataacagca attcaagtgc aag                                         23
```

-continued

```
SEQ ID NO: 5              moltype = DNA   length = 25
FEATURE                   Location/Qualifiers
source                    1..25
                          mol_type = other DNA
                          note = Escherichia coli forward primer
                          organism = synthetic construct
SEQUENCE: 5
cgggtgaagg ttatctctat gaact                                        25

SEQ ID NO: 6              moltype = DNA   length = 23
FEATURE                   Location/Qualifiers
source                    1..23
                          mol_type = other DNA
                          note = Japanese encephalitis virus forward primer
                          organism = synthetic construct
SEQUENCE: 6
gtaaacaagg cttcactgat cgt                                          23

SEQ ID NO: 7              moltype = DNA   length = 26
FEATURE                   Location/Qualifiers
source                    1..26
                          mol_type = other DNA
                          note = Enterovirus forward primer
                          organism = synthetic construct
SEQUENCE: 7
tgaaagttcc ataggagata gcgtga                                       26

SEQ ID NO: 8              moltype = DNA   length = 20
FEATURE                   Location/Qualifiers
source                    1..20
                          mol_type = other DNA
                          note = Internal standard forward primer
                          organism = synthetic construct
SEQUENCE: 8
gacttcagca tggcggtgtt                                              20

SEQ ID NO: 9              moltype = DNA   length = 22
FEATURE                   Location/Qualifiers
source                    1..22
                          mol_type = other DNA
                          note = Human herpesvirus 6 forward primer
                          organism = synthetic construct
SEQUENCE: 9
ctatagcagc gcccaatgcc aa                                           22

SEQ ID NO: 10             moltype = DNA   length = 22
FEATURE                   Location/Qualifiers
source                    1..22
                          mol_type = other DNA
                          note = Varicella-zoster virus forward primer
                          organism = synthetic construct
SEQUENCE: 10
ctcacgtcta tccttattcc ca                                           22

SEQ ID NO: 11             moltype = DNA   length = 21
FEATURE                   Location/Qualifiers
source                    1..21
                          mol_type = other DNA
                          note = Nipah virus forward primer
                          organism = synthetic construct
SEQUENCE: 11
agcaggaagc cagttgatcc a                                            21

SEQ ID NO: 12             moltype = DNA   length = 24
FEATURE                   Location/Qualifiers
source                    1..24
                          mol_type = other DNA
                          note = Powassan virus forward primer
                          organism = synthetic construct
SEQUENCE: 12
agacacaaca gcgtttgggc aaca                                         24

SEQ ID NO: 13             moltype = DNA   length = 21
FEATURE                   Location/Qualifiers
source                    1..21
                          mol_type = other DNA
                          note = West Nile virus forward primer
                          organism = synthetic construct
SEQUENCE: 13
```

-continued

```
ggctgggaga tttagcatca c                                                    21

SEQ ID NO: 14            moltype = DNA   length = 21
FEATURE                  Location/Qualifiers
source                   1..21
                         mol_type = other DNA
                         note = Herpes simplex virus type 1 forward primer
                         organism = synthetic construct
SEQUENCE: 14
gcgcgaccga cagcactcac a                                                    21

SEQ ID NO: 15            moltype = DNA   length = 23
FEATURE                  Location/Qualifiers
source                   1..23
                         mol_type = other DNA
                         note = Herpes simplex virus type 2 forward primer
                         organism = synthetic construct
SEQUENCE: 15
ccttgttttc gaccggcacc cta                                                  23

SEQ ID NO: 16            moltype = DNA   length = 20
FEATURE                  Location/Qualifiers
source                   1..20
                         mol_type = other DNA
                         note = Cryptococcus neoformans forward primer
                         organism = synthetic construct
SEQUENCE: 16
atctctctgc atccgtgaca                                                      20

SEQ ID NO: 17            moltype = DNA   length = 23
FEATURE                  Location/Qualifiers
source                   1..23
                         mol_type = other DNA
                         note = Haemophilus influenzae reverse primer
                         organism = synthetic construct
SEQUENCE: 17
aatatgcagc ttcatcatga cct                                                  23

SEQ ID NO: 18            moltype = DNA   length = 21
FEATURE                  Location/Qualifiers
source                   1..21
                         mol_type = other DNA
                         note = Streptococcus pneumoniae reverse primer
                         organism = synthetic construct
SEQUENCE: 18
cccctaaaat aaccgccttc a                                                    21

SEQ ID NO: 19            moltype = DNA   length = 21
FEATURE                  Location/Qualifiers
source                   1..21
                         mol_type = other DNA
                         note = Neisseria meningitidis reverse primer
                         organism = synthetic construct
SEQUENCE: 19
cttccgtcag actgagttgc c                                                    21

SEQ ID NO: 20            moltype = DNA   length = 23
FEATURE                  Location/Qualifiers
source                   1..23
                         mol_type = other DNA
                         note = Listeria monocytogenes reverse primer
                         organism = synthetic construct
SEQUENCE: 20
caatcaaatg tagttggtcc gtt                                                  23

SEQ ID NO: 21            moltype = DNA   length = 25
FEATURE                  Location/Qualifiers
source                   1..25
                         mol_type = other DNA
                         note = Escherichia coli reverse primer
                         organism = synthetic construct
SEQUENCE: 21
aaagccagta aagtagaacg gtttg                                                25

SEQ ID NO: 22            moltype = DNA   length = 21
FEATURE                  Location/Qualifiers
source                   1..21
                         mol_type = other DNA
                         note = Japanese encephalitis virus reverse primer
```

```
                        organism = synthetic construct
SEQUENCE: 22
tgttctccca atcgctttgc t                                               21

SEQ ID NO: 23           moltype = DNA   length = 24
FEATURE                 Location/Qualifiers
source                  1..24
                        mol_type = other DNA
                        note = Enterovirus reverse primer
                        organism = synthetic construct
SEQUENCE: 23
cttgcctgta tccaatcgat gact                                            24

SEQ ID NO: 24           moltype = DNA   length = 24
FEATURE                 Location/Qualifiers
source                  1..24
                        mol_type = other DNA
                        note = Internal standard reverse primer
                        organism = synthetic construct
SEQUENCE: 24
tagcaacaac tgaatagcca aggt                                            24

SEQ ID NO: 25           moltype = DNA   length = 23
FEATURE                 Location/Qualifiers
source                  1..23
                        mol_type = other DNA
                        note = Human herpesvirus 6 reverse primer
                        organism = synthetic construct
SEQUENCE: 25
gcacctcctt tgtatgtcga ctc                                             23

SEQ ID NO: 26           moltype = DNA   length = 21
FEATURE                 Location/Qualifiers
source                  1..21
                        mol_type = other DNA
                        note = Varicella-zoster virus reverse primer
                        organism = synthetic construct
SEQUENCE: 26
accgtatccg cgtataacag t                                               21

SEQ ID NO: 27           moltype = DNA   length = 26
FEATURE                 Location/Qualifiers
source                  1..26
                        mol_type = other DNA
                        note = Nipah virus reverse primer
                        organism = synthetic construct
SEQUENCE: 27
cacattgcag tttcccttca tcgata                                          26

SEQ ID NO: 28           moltype = DNA   length = 22
FEATURE                 Location/Qualifiers
source                  1..22
                        mol_type = other DNA
                        note = Powassan virus reverse primer
                        organism = synthetic construct
SEQUENCE: 28
tcaagtagcc agtcactcac cg                                              22

SEQ ID NO: 29           moltype = DNA   length = 24
FEATURE                 Location/Qualifiers
source                  1..24
                        mol_type = other DNA
                        note = West Nile virus reverse primer
                        organism = synthetic construct
SEQUENCE: 29
cgacagtcat cacatagtat gcac                                            24

SEQ ID NO: 30           moltype = DNA   length = 23
FEATURE                 Location/Qualifiers
source                  1..23
                        mol_type = other DNA
                        note = Herpes simplex virus type 1 reverse primer
                        organism = synthetic construct
SEQUENCE: 30
gcgtaacacg tacaccccgg cat                                             23

SEQ ID NO: 31           moltype = DNA   length = 21
FEATURE                 Location/Qualifiers
source                  1..21
```

-continued

```
                      mol_type = other DNA
                      note = Herpes simplex virus type 2 reverse primer
                      organism = synthetic construct
SEQUENCE: 31
gacacccagg accaggttcg t                                              21

SEQ ID NO: 32         moltype = DNA   length = 21
FEATURE               Location/Qualifiers
source                1..21
                      mol_type = other DNA
                      note = Cryptococcus neoformans reverse primer
                      organism = synthetic construct
SEQUENCE: 32
cttaagttca gcgggtagtc c                                              21
```

COMPOSITION FOR DETECTING PATHOGENS, AND KIT AND METHOD THEREFOR

CROSS-REFERENCE TO RELATED APPLICATIONS

This application is a continuation of International Application No. PCT/CN2020/096941, filed on Jun. 19, 2020, which claims priority to Chinese Patent Application No. 202010177556.3, filed on Mar. 13, 2020. The disclosures of the aforementioned applications are hereby incorporated by reference in their entireties.

TECHNICAL FIELD

The present invention belongs to the field of detection based on molecular biology, and specifically relates to a composition for detecting, in particular, multiple encephalitis/meningitis/respiratory tract pathogens by using a single-channel multiple real-time fluorescent PCR technique. Furthermore, the present invention also relates to a related kit and a method for using the kit.

BACKGROUND

Encephalitis and meningitis (brain fever) are diseases of the brain infected by pathogens, and are differentiated by different infected brain parts, where the meningitis involves the meninges or meninx infected by pathogens. They are often accompanied by complications of bacterial or viral infections, such as ear, sinus or upper respiratory infections. The pathogens causing the encephalitis and/or the meningitis are diverse, the scopes and degrees of lesions vary widely, and the clinical manifestations are very complex.

At present, there are many clinical methods for detecting encephalitis and/or meningitis pathogens, such as a direct imaging and biopsy etiological examination method, an EEG-assisted diagnosis method, an imaging examination method, an immunological examination method, a cytological examination method, a gene chip method and a PCR detection method. However, these known methods have many shortcomings, such as great time consumption, unacceptable sampling methods, low diagnostic efficiency or inability to make definite diagnoses, low sensitivity and sample pollution risks.

Especially with the rapid development of molecular diagnostic technology, new techniques such as PCR, RT-PCR, Real-Time PCR and LAMP are slowly replacing traditional low-sensitivity, time-consuming and laborious detection methods such as pathogen isolation and culture and biochemical identification, by virtue of their high specificity, sensitivity and timeliness. However, the sensitivity of clinical diagnosis includes not only analytical sensitivity (AS), but also clinical sensitivity (CS). For example, respiratory infections may be caused by 30-40 common pathogens. If only one indication is detected, the CS will be greatly reduced no matter how high the AS is. Therefore, compared with PCR techniques that can detect only one pathogen at a time, multiple PCR techniques have been paid increasingly more attention in the field of molecular diagnosis because of their characteristics of high throughput, high efficiency, low costs and less time consumption. The multiple PCR techniques can enable molecular diagnosis to not only expose issues from one aspect, but also acquire information from all aspects, thereby increasing the sensitivity of clinical diagnosis.

Fluorescent quantitative PCR has developed rapidly in the past 20 years and has penetrated into all fields of biotechnology development. Existing common fluorescent quantitative instruments have four to five detection channels, and therefore the number of target genes detected in a single tube is usually also four to five, which has also become a bottleneck of multiple real-time quantitative PCR detection. Moreover, in the development of using a finite number of detection channels in one reaction tube to improve the throughput of target detection, multi-target detection for increasingly complex compound pathogen infection and polygenic genetic disease diagnosis also needs to be confronted with. In multiple PCR amplification, the challenge of further optimization of PCR reaction systems each time a pair of primers is added further needs to be faced.

Therefore, in the detection of multiple encephalitis/meningitis/respiratory tract pathogens, it is desired to develop single-color, single-channel and multi-target detection and optimize a PCR reaction system without changing hardware facilities of existing fluorescent quantitative PCR instruments in the market, so as to develop a set of mature techniques that enables detection based on multi-target amplification.

SUMMARY

The present invention is intended to overcome at least some defects existing in the prior art. The present invention is developed based at least in part on the inventor's idea of carrying out a melting curve analysis method according to different Tm values of fluorescence products used by multiple targets in a single channel, and determining negative and positive test results according to whether there is a characteristic peak in a melting curve, thereby increasing the detection throughput of a single-tube reaction by four times.

Accordingly, in a first aspect, the present application provides a composition, including:

- a primer pair for *Haemophilus influenzae*, sequences of which are respectively as shown in SEQ ID NO: 1 and SEQ ID NO: 17;
- a primer pair for *Streptococcus pneumoniae*, sequences of which are respectively as shown in SEQ ID NO: 2 and SEQ ID NO: 18;
- a primer pair for *Neisseria meningitidis*, sequences of which are respectively as shown in SEQ ID NO: 3 and SEQ ID NO: 19;
- a primer pair for *Listeria monocytogenes*, sequences of which are respectively as shown in SEQ ID NO: 4 and SEQ ID NO: 20;
- a primer pair for *Escherichia coli*, sequences of which are respectively as shown in SEQ ID NO: 5 and SEQ ID NO: 21;
- a primer pair for Japanese encephalitis virus, sequences of which are respectively as shown in SEQ ID NO: 6 and SEQ ID NO: 22;
- a primer pair for an enterovirus, sequences of which are respectively as shown in SEQ ID NO: 7 and SEQ ID NO: 23;
- a primer pair for human herpesvirus 6, sequences of which are respectively as shown in SEQ ID NO: 9 and SEQ ID NO: 25;
- a primer pair for varicella-zoster virus, sequences of which are respectively as shown in SEQ ID NO: 10 and SEQ ID NO: 26;
- a primer pair for Nipah virus, sequences of which are respectively as shown in SEQ ID NO: 11 and SEQ ID NO: 27;

a primer pair for Powassan virus, sequences of which are respectively as shown in SEQ ID NO: 12 and SEQ ID NO: 28;

a primer pair for West Nile virus, sequences of which are respectively as shown in SEQ ID NO: 13 and SEQ ID NO: 29;

a primer pair for Herpes simplex virus type 1, sequences of which are respectively as shown in SEQ ID NO: 14 and SEQ ID NO: 30;

a primer pair for Herpes simplex virus type 2, sequences of which are respectively as shown in SEQ ID NO: 15 and SEQ ID NO: 31; and a primer pair for *Cryptococcus neoformans*, sequences of which are respectively as shown in SEQ ID NO: 16 and SEQ ID NO: 32.

In some embodiments, sequences SEQ ID NO: 1 to SEQ ID NO: 16 carry fluorescent reporter groups.

In some embodiments, the sequences SEQ ID NO: 1 to SEQ ID NO: 16 carry fluorescence quenching groups, and further the fluorescent reporter group and the fluorescence quenching group are spaced apart by 15-25 nt.

Thus, with the foregoing composition of the present invention, 15 particular pathogens may be detected and analyzed at the same time in one experiment, so as to provide a rapid molecular diagnosis solution for clinical practice and disease control and monitoring. These 15 pathogens may be used to assist in the diagnosis of encephalitis, meningitis and respiratory infections.

In specific embodiment, sequences SEQ ID NO: 1 to SEQ ID NO: 4 have a first fluorescent reporter group; sequences SEQ ID NO: 5 to SEQ ID NO: 7 have a second fluorescent reporter group; sequences SEQ ID NO: 9 to SEQ ID NO: 12 have a third fluorescent reporter group; and sequences SEQ ID NO: 13 to SEQ ID NO: 16 have a fourth fluorescent reporter group, where the first fluorescent reporter group, the second fluorescent reporter group, the third fluorescent reporter group and the fourth fluorescent reporter group are different from one another.

The composition introduces specific primer and fluorescent primer sequences for amplifying *Haemophilus influenzae* (HI), *Streptococcus pneumoniae* (SP), *Neisseria meningitidis* (NM), *Listeria monocytogenes* (LM), *Escherichia coli* (ECO), Japanese encephalitis virus (JEV), the enterovirus (EV), human herpesvirus 6 (HHV6), varicella-zoster virus (VZV), Nipah virus (NVD), Powassan virus (POWV), West Nile virus (WNV), Herpes simplex virus type 1 (HSV-1), Herpes simplex virus type 2 (HSV-2) and *Cryptococcus neoformans* (CN), as shown in SEQ ID NOs: 1-7, 9-23 and 25-32. However, it should be known that the composition of the present invention may further include specific primer pairs for amplifying pathogens other than the above 15 particular pathogens.

In some embodiments, the first fluorescent reporter group, the second fluorescent reporter group, the third fluorescent reporter group and the fourth fluorescent reporter group may be independently selected from, but is not limited to, FAM, HEX, ROX, CY5, VIC, JOE and TAMRA. In some embodiments, the first fluorescent reporter group is FAM, the second fluorescent reporter group is HEX, the third fluorescent reporter group is ROX, and the fourth fluorescent reporter group is CY5.

In some embodiments, products amplified by primer sequences with the same fluorescent reporter group are designed to show a characteristic Tm value at different temperatures; products amplified by primer sequences with different fluorescent reporter groups are designed to show a characteristic Tm value at the same corresponding temperature. Specifically, in the present application, products amplified by the primer sequences with the first fluorescent reporter group show a melting curve peak at a first temperature, a second temperature, a third temperature and a fourth temperature respectively; products amplified by the primer sequences with the second fluorescent reporter group show a melting curve peak at the first temperature, the second temperature, the third temperature and the fourth temperature respectively; products amplified by the primer sequences with the third fluorescent reporter group show a melting curve peak at the first temperature, the second temperature, the third temperature and the fourth temperature respectively; products amplified by the primer sequences with the fourth fluorescent reporter group show a melting curve peak at the first temperature, the second temperature, the third temperature and the fourth temperature respectively, where the first temperature, the second temperature, the third temperature and the fourth temperature are different from one another.

In some embodiments, the molar ratio of sequences SEQ ID NOs: 1-7 and 9-16 to sequences SEQ ID NOs: 17-23 and 25-32 is 1:2-2:1, further 1:0.95-0.85, further 1:0.9.

In some embodiments, the composition of the present invention may further include an internal standard. An exemplary internal standard includes, but is not limited to, a human endogenous housekeeping gene (internal standard). In particularly specific embodiment, the composition of the present invention includes a primer pair for the exemplary internal standard, sequences of which are respectively as shown in SEQ ID NO: 8 and SEQ ID NO: 24.

In some embodiments, SEQ ID NO: 8 may carry the first, second, third or fourth fluorescent reporter group and may carry the fluorescence quenching group, further may carry the second fluorescent reporter group, and further may show a melting curve peak at the fourth temperature.

It should be understood that in the present invention, the expressions "first" and "second" are only used for purpose of description to distinguish the defined substances, temperature and the like, without defining the order or priority in any way.

In a second aspect, the present application provides a kit, which includes the composition of the present invention.

In some embodiments, the kit further includes a reagent for extracting a sample, and further the sample is a cerebrospinal fluid. In some embodiments, the kit further includes a DNA/RNA extraction reagent (Tris-HCl, NaCl, KCl, Tween 20, Triton X-100), dNTPs (20-200 μmol/L), $Mg^{2+}$ (1.5-3 mmol/L), a Taq polymerase (0.5-5 U/100 μL, pH 8.3-8.5), and a PCR buffer solution (100 mmol/LTris-HCl, pH 8.3; 250 mmol/L KCl; $Mg^{2+}$).

In a third aspect, the present application provides a method for detecting a pathogen, which includes:

providing a sample to undergo detection;

adding the composition of the present invention or the kit of the present invention to the sample to undergo detection, so as to perform amplification by PCR;

acquiring a change in fluorescence signal intensity, especially a change in fluorescence signal intensity of an amplification product of a specific primer to generate a melting curve, so as to qualitatively analyze a detected target sequence.

In some embodiments, the melting curve is analyzed at 50° C. to 95° C., and fluorescence is collected once with every rise of 0.5° C.

In the present invention, by designing particular specific primers, after amplification with fluorescent primers, fluorescent products have different Tm values, so as to detect and analyze multiple targets, for example, four targets, in a single-color fluorescence channel at the same time. In this way, the present invention may detect 15 particular pathogens, break through the bottleneck that one sample in a single test may give detection information of only four targets, improve the throughput and efficiency of clinical nucleic acid detection, and provide a simple and efficient detection method for multiple pathogen detection and large syndrome monitoring in clinical practice and scientific research. In addition, the melting curve method adopts the way of nucleic acid hybridization, which has better specificity and higher sensitivity. More importantly, the whole detection process is carried out under single-tube closed conditions, which avoid false positives and environmental pollution caused by crossover between samples.

DETAILED DESCRIPTION OF EMBODIMENTS

Figure 1:
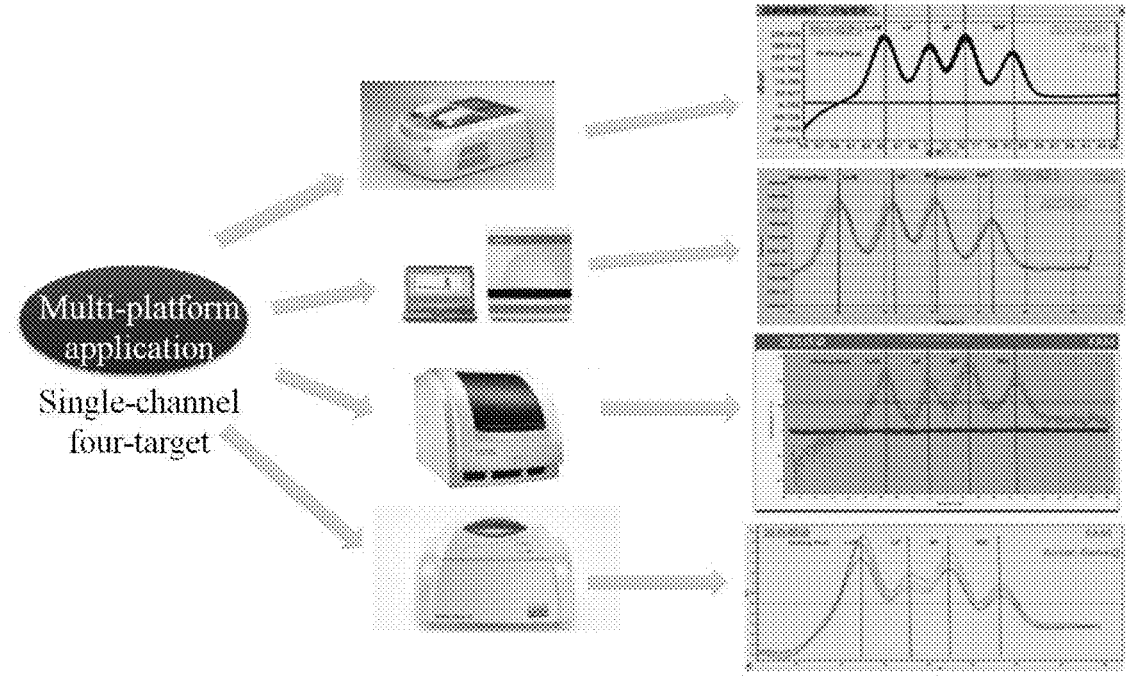
FIG. 1 illustrates a schematic diagram of multi-platform application of the composition according to the present invention.

Generally speaking, with the present invention, multiple pathogens, especially 15 particular pathogens, may be detected at the same time in the same tube containing reagents. Thus, more target detection information may be provided for a doctor in one test for a nucleic acid sample, especially those difficult to sample such as a cerebrospinal fluid. In addition, in the present invention, the whole process of PCR amplification and product analysis is carried out under single-tube closed conditions, reducing pollution in molecular detection and allowing real-time monitoring of the reaction process.

More specifically, based on the technical principle of generation of fluorescence signals through hybridization of fluorescent products after amplification of fluorescent primers, four targets are amplified at the same time according to different Tm values of products by using a melting curve in a single-color fluorescence channel, so as to detect and analyze the four targets in the single-color fluorescence channel.

The present invention will be described in detail below in conjunction with specific embodiments and examples. The advantages and various effects of the present invention will be presented more clearly therefrom. Those skilled in the art should understand that these specific embodiments and examples are intended to describe the present invention, instead of limiting the present invention.

In the following, unless otherwise specified, all reagents, instruments, and the like are commercially available.

Example 1

Sequences 30 primer sequences and 2 internal standard sequences: SEQ ID NO: 01-SEQ. ID NO: 32 were used, in which SEQ. ID NO: 08 and SEQ ID NO: 24 were an internal standard primer pair.

SEQ ID NOs: 1-7, 9-23 and 25-32 were used for specifically detecting *Haemophilus influenzae* (HI), *Streptococcus pneumoniae* (SP), *Neisseria meningitidis* (NM), *Listeria monocytogenes* (LM), *Escherichia coli* (ECO), Japanese encephalitis virus (JEV), an enterovirus (EV), human herpesvirus 6 (HHV6), varicella-zoster virus (VZV), Nipah virus (NVD), Powasen virus (POWV), West Nile virus (WNV), Herpes simplex virus type 1 (HSV-1), Herpes simplex virus type 2 (HSV-2) and *Cryptococcus neoformans* (CN).

TABLE 1

| Primer and internal standard sequences | |
| --- | --- |
| BHQ1-CACCAGAATACAACA(T-FAM)CGCATT | SEQ. ID NO: 01 |
| BHQ1-AACCACGAGTAAGAG(T-FAM)GATGA | SEQ. ID NO: 02 |
| BHQ1-AATTCTGCCGTAAGCCGCA(T-FAM)C | SEQ. ID NO: 03 |
| BHQ1-AATAACAGCAATTCAAG(T-FAM)GCAAG | SEQ. ID NO: 04 |
| BHQ1-CGGGTGAAGGTTATCTCTA(T-HEX)GAACT | SEQ. ID NO: 05 |
| BHQ1-GTAAACAAGGCTTCACTGA(T-HEX)CGT | SEQ. ID NO: 06 |
| BHQ1-TGAAAGTTCCATAGGAGATAGCG(T-HEX)GA | SEQ. ID NO: 07 |
| BHQ1-GACTTCAGCATGGCGGTG(T-HEX)T | SEQ. ID NO: 08 |
| BHQ2-CTATAGCAGCGCCCAA(T-ROX)GCCAA | SEQ. ID NO: 09 |
| BHQ2-CTCACGTCTATCCTTAT(T-ROX)CCCA | SEQ. ID NO: 10 |
| BHQ2-AGCAGGAAGCCAGTTGA(T-ROX)CCA | SEQ. ID NO: 11 |
| BHQ2-AGACACAACAGCGTT(T-ROX)GGGCAACA | SEQ. ID NO: 12 |
| BHQ2-GGCTGGGAGATTTAGCA(T-CY5)CAC | SEQ. ID NO: 13 |
| BHQ2-GCGCGACCGACAGCAC(T-CY5)CACA | SEQ. ID NO: 14 |
| BHQ2-CCTTGTTTTCGACCGGCACCC(T-CY5)A | SEQ. ID NO: 15 |
| BHQ2-ATCTCTCTGCATCCG(T-CY5)GACA | SEQ. ID NO: 16 |
| AATATGCAGCTTCATCATGACCT | SEQ. ID NO: 17 |
| CCCCTAAAATAACCGCCTTCA | SEQ. ID NO: 18 |
| CTTCCGTCAGACTGAGTTGCC | SEQ. ID NO: 19 |
| CAATCAAATGTAGTTGGTCCGTT | SEQ. ID NO: 20 |
| AAAGCCAGTAAAGTAGAACGGTTTG | SEQ. ID NO: 21 |
| TGTTCTCCCAATCGCTTTGCT | SEQ. ID NO: 22 |
| CTTGCCTGTATCCAATCGATGACT | SEQ. ID NO: 23 |
| TAGCAACAACTGAATAGCCAAGGT | SEQ. ID NO: 24 |
| GCACCTCCTTTGTATGTCGACTC | SEQ. ID NO: 25 |
| ACCGTATCCGCGTATAACAGT | SEQ. ID NO: 26 |
| CACATTGCAGTTTCCCTTCATCGATA | SEQ. ID NO: 27 |

TABLE 1-continued

| Primer and internal standard sequences | | |
| --- | --- | --- |
| TCAAGTAGCCAGTCACTCACCG | SEQ. ID NO: | 28 |
| CGACAGTCATCACATAGTATGCAC | SEQ. ID NO: | 29 |
| GCGTAACACGTACACCCCGGCAT | SEQ. ID NO: | 30 |
| GACACCCAGGACCAGGTTCGT | SEQ. ID NO: | 31 |
| CTTAAGTTCAGCGGGTAGTCC | SEQ. ID NO: | 32 |

Example 2

DNA/RNA Extraction

DNA/RNA was extracted by adopting a paramagnetic particle method. The following operations were carried out in a sample treatment room:

An appropriate number of 1.5-mL sterilized centrifuge tubes were taken, which were respectively labeled a negative control, a positive control and a sample to undergo detection, respectively. 300 μL of a DNA/RNA extraction solution was added to each tube.

200 μL of the sample to undergo detection, the negative control or the positive control was added to each tube. The tube was covered with a cap, and shaken for 10 seconds for through mixing, and subjected to a short spin.

100 μL of a DNA/RNA extraction solution 2-mix was added to each tube by sucking up after through mixing, and the tube was shaken for 10 seconds for through mixing, and left to stand for 10 minutes at room temperature.

After the short spin, the centrifuge tubes were placed on a separator, and the solution was sucked out slowly after 3 minutes (pay attention not to touch the brown substance adhered to the tube wall).

600 μL of a DNA/RNA extraction solution 3 and 200 μL of a DNA/RNA extraction solution 4 were added to each tube, and the tube was shaken for 5 seconds for through mixing and subjected to a short spin, and then the centrifuge tube was placed on the separator again.

After about 3 minutes, the supernatant separated into two layers. A pipette tip was inserted into the bottom of the centrifuge tube, the liquid was slowly sucked up from the bottom and completely discarded. The tube was left to stand for 1 minute and then the residual liquid at the bottom of the tube was completely sucked up and discarded.

Example 3

PCR Reaction

50 μL of PCR-mix ($Mg^{2+}$, dNTPs, MMLV, Taq enzyme, primer, PCR buffer solution) was added to each tube. The PCR-mix was sucked up with a pipette tip to elute the brown residue adhered to the wall of the centrifuge tube. The operation was repeated several times to elute the residue as completely as possible, and then all the eluted brown mixture was transferred to a 0.2-mL PCR reaction tube, and the tube was covered with a cap and transferred to an amplification test region.

The following analysis was carried out by using a Hongshi SLAN-96P full-automatic medical PCR analysis system.

A fluorescent PCR reaction system was as shown in Table 2. A PCR amplification procedure was as shown in Table 3.

TABLE 2

| PCR reaction system | |
| --- | --- |
| Component | Volume/concentration in each reaction |
| $Mg^{2+}$ | 4 mM |
| dNTPs (100 mM) | 0.25 mM |
| MMLV(10 U/μL) | 10U |
| Taq enzyme 5 U/μL) | 5U |
| SEQ ID NOs: 1-16 | 100 nM |
| SEQ ID NOs: 16-32 | 50 nM |
| PCR buffer solution (1.5x) | Up to 50 μL |

TABLE 3

| PCR amplification procedure | | | |
| --- | --- | --- | --- |
| Step | Temperature | Time | Number of cycles |
| Reverse transcription | 50° C. | 30 min | 1 |
| Pre-denaturation | 94° C. | 5 min | 1 |
| Denaturation | 94° C. | 15 s | 45 |
| Annealing | 60° C. | 30 s | |
| Melting curve analysis | 50° C. to 95° C. | Fluorescence is collected once with every rise of 0.5° C. | 1 |

Example 4

A positive plasmid of each target was used as a template to simulate a clinical sample. Multiple PCR tests were carried out on a Hongshi fluorescent quantitative PCR instrument.

Based on the technical principle of generation of fluorescence signals through hybridization of products after amplification of fluorescent primers, a target was detected by adopting a melting curve method. Whether there was a characteristic peak at Tm was used as a criterion for determining negative and positive test results. If there was a characteristic peak at a specific Tm temperature, the test result was positive; if not, the test result was negative.

In the exemplary example, exemplarily, the first temperature may be roughly set to 67° C.±1° C.; the second temperature may be roughly set to 71° C.±1° C.; the third temperature may be roughly set to 75° C.±1° C.; the fourth temperature may be roughly set to 81° C.±1° C. Exemplarily, melting curve peaks of the targets HI, ECO, HHV6 and WNV may be set to the first temperature, i.e., 67° C.±1° C.; melting curve peaks of the targets SP, JEV, VZV and HSV1 may be set to the second temperature, i.e., 71° C.±1° C.; melting curve peaks of the targets NM, EV, NVD and HSV2 may be set to the third temperature, i.e., 75° C.±1° C.; melting curve peaks of the targets LM, POWV and CN may be set to the fourth temperature, i.e., 81° C.±1° C.; and a melting curve peak of the internal standard IC may be set to the fourth temperature.

Figure 2:
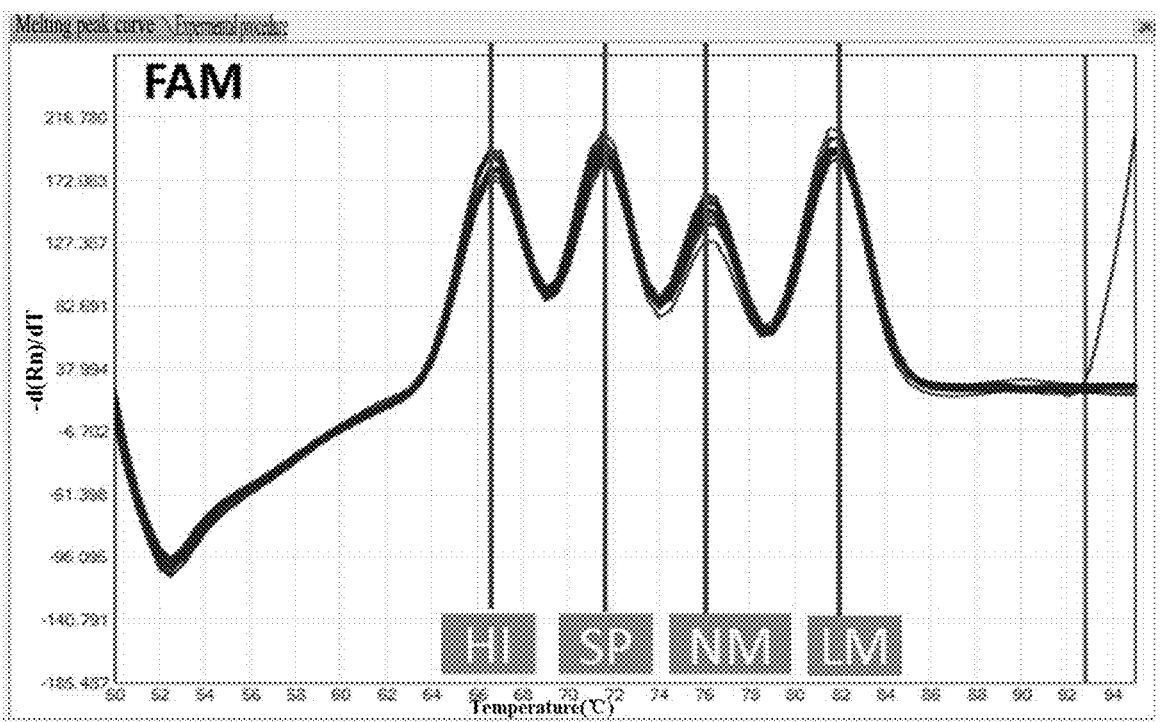
FIG. 2 illustrates a positive test result in a FAM channel according to an example of the present invention.
Figure 3:
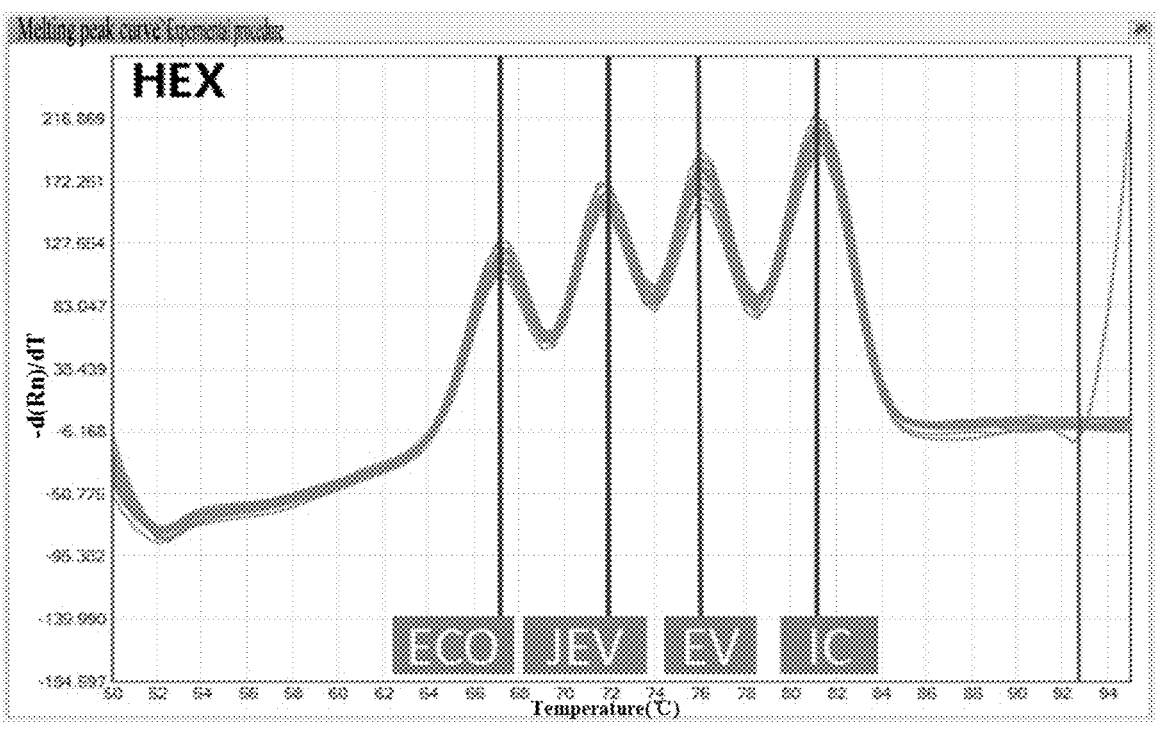
FIG. 3 illustrates a positive test result in a HEX channel according to an example of the present invention.
Figure 4:
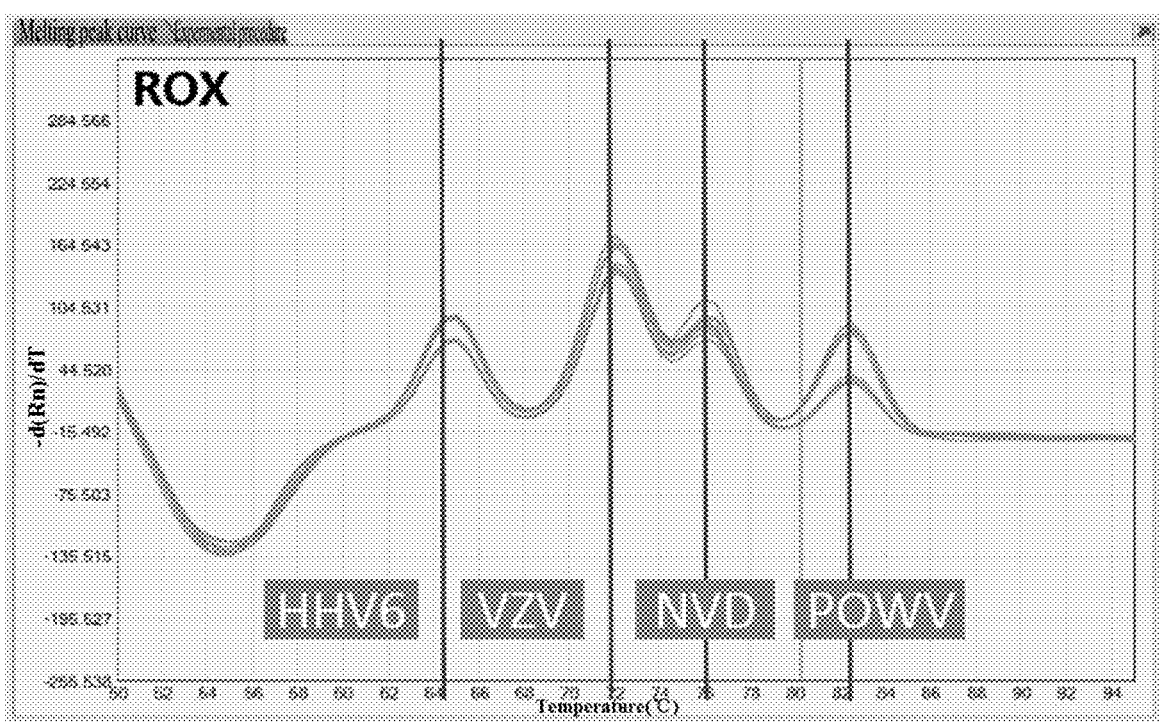
FIG. 4 illustrates a positive test result in a ROX channel according to an example of the present invention.
Figure 5:
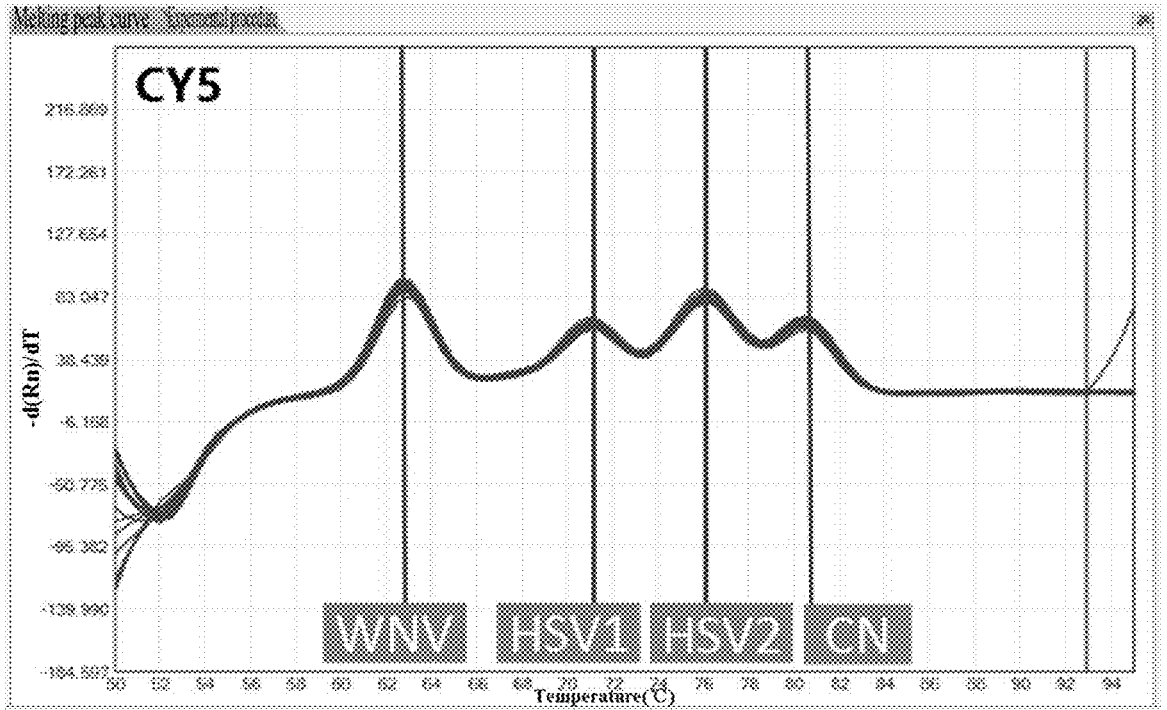
FIG. 5 illustrates a positive test result in a CY5 channel according to an example of the present invention.

Target detection signals were FAM, HEX, ROX and CY5. Results were as shown in FIG. 2 to FIG. 5.
Result Analysis
A. FAM channel (refer to FIG. 2):
A melting curve peak appeared at the temperature of about 67° C., which confirmed the presence of the pathogen *Haemophilus influenzae* (HI).

A melting curve peak appeared at the temperature of about 71.5° C., which confirmed the presence of the pathogen *Streptococcus pneumoniae* (SP).

A melting curve peak appeared at the temperature of about 76.5° C., which confirmed the presence of the pathogen *Neisseria meningitidis* (NM).

A melting curve peak appeared at the temperature of about 82° C., which confirmed the presence of the pathogen *Listeria monocytogenes* (LM).

B. HEX channel (refer to FIG. 3):

A melting curve peak appeared at the temperature of about 67.1° C., which confirmed the presence of the pathogen *Escherichia coli* (ECO).

A melting curve peak appeared at the temperature of about 71.8° C., which confirmed the presence of the pathogen Japanese encephalitis virus (JEV).

A melting curve peak appeared at the temperature of about 76.3° C., which confirmed the presence of the pathogen enterovirus (EV).

A melting curve peak appeared at the temperature of about 81.5° C., which confirmed that the internal standard was positive.

C. ROX channel (refer to FIG. 4):

A melting curve peak appeared at the temperature of about 64.9° C., which confirmed the presence of the pathogen human herpesvirus 6 (HHV6).

A melting curve peak appeared at the temperature of about 71.9° C., which confirmed the presence of the pathogen varicella-zoster virus (VZV).

A melting curve peak appeared at the temperature of about 76.2° C., which confirmed the presence of the pathogen Nipah virus (NVD).

A melting curve peak appeared at the temperature of about 82.2° C., which confirmed the presence of the pathogen Powassan virus (POWV).

D. CY5 channel (refer to FIG. 5):

A melting curve peak appeared at the temperature of about 63.9° C., which confirmed the presence of the pathogen West Nile virus (WNV).

A melting curve peak appeared at the temperature of about 71.1° C., which confirmed the presence of the pathogen Herpes simplex virus type 1 (HSV-1).

A melting curve peak appeared at the temperature of about 76.1° C., which confirmed the presence of the pathogen Herpes simplex virus type 2 (HSV-2).

A melting curve peak appeared at the temperature of about 80.8° C., which confirmed the presence of the pathogen *Cryptococcus neoformans* (CN).

Although the present invention has been described in detail with reference to examples of the present invention, these examples are provided for describing, instead of limiting the present invention. Other examples that can be obtained according to the principle of the present invention still belong to the scope defined by the claims of the present invention.

REFERENCE TO AN ELECTRONIC SEQUENCE LISTING

The contents of the electronic sequence listing (CU700SequenceListing.xml; Size: 35,412 bytes; and Date of Creation: Sep. 2, 2022) is herein incorporated by reference in its entirety.

---

What is claimed is:

1. A composition, comprising:
a primer pair for *Haemophilus influenzae*, sequences of which are SEQ ID NO: 1 and SEQ ID NO: 17;
a primer pair for *Streptococcus pneumoniae*, sequences of which are SEQ ID NO: 2 and SEQ ID NO: 18;
a primer pair for *Neisseria meningitidis*, sequences of which are SEQ ID NO: 3 and SEQ ID NO: 19;
a primer pair for *Listeria monocytogenes*, sequences of which are SEQ ID NO: 4 and SEQ ID NO: 20;
a primer pair for *Escherichia coli*, sequences of which are SEQ ID NO: 5 and SEQ ID NO 21;
a primer pair for Japanese encephalitis virus, sequences of which are SEQ ID NO: 6 and SEQ ID NO: 22;
a primer pair for an enterovirus, sequences of which are SEQ ID NO: 7 and SEQ ID NO: 23;
a primer pair for human herpesvirus 6, sequences of which are in SEQ ID NO: 9 and SEQ ID NO: 25;
a primer pair for varicella-zoster virus, sequences of which are in SEQ ID NO: 10 and SEQ ID NO: 26;
a primer pair for Nipah virus, sequences of which are SEQ ID NO: 11 and SEQ ID NO: 27;
a primer pair for Powassan virus, sequences of which are SEQ ID NO: 12 and SEQ ID NO: 28;
a primer pair for West Nile virus, sequences of which are SEQ ID NO: 13 and SEQ ID NO: 29;
a primer pair for Herpes simplex virus type 1, sequences of which are SEQ ID NO: 14 and SEQ ID NO: 30;
a primer pair for Herpes simplex virus type 2, sequences of which are SEQ ID NO: 15 and SEQ ID NO: 31; and
a primer pair for *Cryptococcus neoformans*, sequences of which are SEQ ID NO: 16 and SEQ ID NO: 32;
wherein sequences SEQ ID NOs: 1-7 and 9-16 carry fluorescent reporter groups.

2. The composition according to claim 1, wherein the sequences SEQ ID NOs: 1-7 and 9-16 carry fluorescence quenching groups.

3. The composition according to claim 2, wherein the fluorescent reporter group and the fluorescence quenching group are spaced apart by 15-25 nt.

4. The composition according to claim 1, wherein
sequences SEQ ID NO: 1 to SEQ ID NO: 4 have a first fluorescent reporter group;
sequences SEQ ID NO: 5 to SEQ ID NO: 7 have a second fluorescent reporter group;
sequences SEQ ID NO: 9 to SEQ ID NO: 12 have a third fluorescent reporter group; and
sequences SEQ ID NO: 13 to SEQ ID NO: 16 have a fourth fluorescent reporter group;

wherein the first fluorescent reporter group, the second fluorescent reporter group, the third fluorescent reporter group and the fourth fluorescent reporter group are different from one another.

5. The composition according to claim 4, wherein the first fluorescent reporter group, the second fluorescent reporter group, the third fluorescent reporter group and the fourth fluorescent reporter group are independently selected from FAM, HEX, ROX, CY5, VIC, JOE and TAMRA.

6. The composition according to claim 5, wherein the first fluorescent reporter group is FAM, the second fluorescent reporter group is HEX, the third fluorescent reporter group is ROX, and the fourth fluorescent reporter group is CY5.

7. The composition according to claim 1, wherein molar ratio of sequences SEQ ID NOs: 1-7 and 9-16 to sequences SEQ ID NOs: 17-23 and 25-32 is 1:2-2:1.

8. The composition according to claim 7, wherein the molar ratio of sequences SEQ ID NOs: 1-7 and 9-16 to sequences SEQ ID NOs: 17-23 and 25-32 is 1:0.95-0.85.

9. The composition according to claim 7, wherein the molar ratio of sequences SEQ ID NOs: 1-7 and 9-16 to sequences SEQ ID NOs: 17-23 and 25-32 is 1:0.9.

10. The composition according to claim 1, wherein the composition further includes an internal standard.

11. The composition according to claim 10, wherein the internal standard includes a human endogenous housekeeping gene.

12. The composition according to claim 10, wherein the composition includes a primer pair for the internal standard, sequences of which are SEQ ID NO: 8 and SEQ ID NO: 24.

13. A kit, comprising the composition according to claim 1.

14. The kit according to claim 13, wherein the kit further comprises a reagent for extracting a sample.

15. The kit according to claim 14, wherein the sample is a cerebrospinal fluid.

16. The kit according to claim 13, wherein the kit further includes a DNA/RNA extraction reagent, dNTPs, $Mg^2+$, a Taq polymerase, and a PCR buffer solution.

17. A method for detecting a pathogen, wherein the method comprises:
providing a sample to undergo detection;
adding the composition according to claim 1 to the sample to undergo detection, so as to perform amplification by PCR; and
acquiring a change in fluorescence signal intensity to generate a melting curve, so as to qualitatively analyze a detected target sequence.

18. The method according to claim 17, wherein the melting curve is analyzed at 50° C. to 95° C., and fluorescence is collected once with every rise of 0.5° C.

19. The method according to claim 17, wherein the fluorescence signal intensity is a fluorescence signal intensity of an amplification product of a specific primer.

* * * * *